US009421375B2

(12) United States Patent
Tscherch et al.

(10) Patent No.: US 9,421,375 B2
(45) Date of Patent: Aug. 23, 2016

(54) SENSING UNIT FOR A TISSUE STIMULATOR

(71) Applicant: BIOTRONIK SE & CO. KG, Berlin (DE)

(72) Inventors: Frank Tscherch, Bestensee (DE); Christian Kreidler, Berlin (DE); Thomas Kiefer, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 0 days.

(21) Appl. No.: 14/512,492

(22) Filed: Oct. 13, 2014

(65) Prior Publication Data
US 2015/0119949 A1   Apr. 30, 2015

Related U.S. Application Data

(60) Provisional application No. 61/896,138, filed on Oct. 28, 2013.

(51) Int. Cl.
*A61N 1/36* (2006.01)
*A61N 1/39* (2006.01)
*A61N 1/362* (2006.01)
*A61N 1/37* (2006.01)

(52) U.S. Cl.
CPC ........... *A61N 1/36125* (2013.01); *A61N 1/362* (2013.01); *A61N 1/3605* (2013.01); *A61N 1/36135* (2013.01); *A61N 1/3704* (2013.01); *A61N 1/3925* (2013.01); *A61N 1/3956* (2013.01)

(58) Field of Classification Search
CPC ..................... A61N 1/36125; A61N 1/3704
See application file for complete search history.

(56) References Cited

U.S. PATENT DOCUMENTS

| 4,148,320 | A | * | 4/1979 | Ohara | A61N 1/3712 607/9 |
| 4,251,831 | A | * | 2/1981 | Kamath | H03H 17/026 348/615 |
| 6,704,602 | B2 | | 3/2004 | Berg et al. | |
| 2007/0146189 | A1 | | 6/2007 | Wesselink et al. | |
| 2011/0066053 | A1 | | 3/2011 | Yazicioglu | |
| 2013/0030486 | A1 | | 1/2013 | Betzold | |

FOREIGN PATENT DOCUMENTS

EP   2294978 A1   3/2011

OTHER PUBLICATIONS

European Search Report received from EP Application Serial No. 14188787, dated Mar. 4, 2015, 4 pages.

* cited by examiner

*Primary Examiner* — Eric D. Bertram
(74) *Attorney, Agent, or Firm* — ARC IP Law, PC; Joseph J. Mayo

(57) ABSTRACT

A tissue stimulator including a sensing unit, wherein the sensing unit includes an A/D converter that samples an analog signal using a sampling clock and converts the analog signal into a digital signal. The tissue stimulator includes a digital filter with an input, wherein the input is connected to an output of the A/D converter. Using a filter clock, the digital filter filters the digital signal, and wherein the filter clock is a multiple of the sampling clock for a specific period of time T.

14 Claims, 3 Drawing Sheets

SENSING UNIT FOR A TISSUE STIMULATOR

This application claims the benefit of U.S. Provisional Patent Application 61/896,138 filed on 28 Oct. 2013, the specification of which is hereby incorporated herein by reference.

BACKGROUND OF THE INVENTION

1. Field of the Invention

Embodiments of the invention generally relate to a sensing unit that processes electrical signals of a human or animal body and specifically enables earlier signal detection after stimulation than known solutions that cannot identify natural activities of the body tissue for a specific period of time after stimulation, e.g., during digital blanking.

2. Description of the Related Art

Sensing units are generally a component of tissue stimulators such as cardiac pacemakers, defibrillators, cardioverters, neurostimulators and the like and are used for the processing of electrical signals of the body tissue, which are normally captured by means of electrodes at, on, or in the tissue. A typical sensing unit is connected via an electrode connection to such an electrode and includes at least one analogue-digital converter (A/D converter) and a digital filter stage. The further processing of the output signals of the sensing unit comprises at least an assessment of the signal amplitudes, for example electrical signals of the body tissue with a amplitude above a specific threshold value are thus identified as natural activity and are assigned to specific physiological events on the basis of their characteristics. For stimulation of the body tissue, the tissue stimulator contains a stimulation unit, via which one or more electric pulses are delivered to the body tissue via the electrode. Since the amplitude of the stimulation pulses is usually a multiple of the amplitudes of the natural electric tissue activity, the connection between the sensing unit and the electrode is interrupted at least for the duration of the stimulation (for example, with a stimulation pulse duration of 1 ms, this time of separation of the sensing unit from the electrode may be 8 to 20 ms).

Generally, stimulation pulses may cause polarization effects (charge reversal effects at the boundary layer between the electrode surface and the electrolyte) at the electrode in the electrolyte or the surrounding tissue and may lead to a step of the amplitude of the input signal of the sensing unit when connected to the electrode after the stimulation. In particular, filters of a sensing unit typically respond to this step in amplitude of the input signal by a step response, which manifests itself as a longer lasting increased amplitude of the output signal of the sensing unit and is also generally referred to as a stimulation artifact. Such stimulation artifacts, generally, may negatively influence the function of the tissue stimulator because a stimulation artifact may be misinterpreted incorrectly as natural electric tissue activity.

Typically, the output signals of the sensing unit are therefore excluded from the signal detection for a specific period of time after the stimulation, also referred to as digital blanking. A disadvantage of excluding the output signals from the signal detection, generally, is that actual natural activities of the body tissue cannot be identified during the period of digital blanking.

As such, in view of the above, there is a need for a sensing unit that overcomes this disadvantage and that enables earlier signal detection after stimulation.

For analog/digital (A/D) conversion, time-continuous analogue signals are normally sampled in the sensing unit at a specific sampling frequency and are converted into digitally coded time-discrete and amplitude-discrete sampling values. The sampling frequency is fed to the A/D converter as a clock frequency. The A/D converter provides a new sampled value with each clock step of the clock frequency. With the subsequent digital filtering, the sampled values are subjected to mathematical operations, such as multiplication and/or addition with filter coefficients in accordance with the selected filter algorithm, wherein the same clock frequency as with the A/D conversion is used. The digital filter thus delivers a modified sampled value at the output with each clock step for the sampled value present at the input.

BRIEF SUMMARY OF THE INVENTION

One or more embodiments of the invention include a sensing unit of a tissue stimulator, wherein the sensing unit includes an A/D converter that samples an analog signal using a sampling clock and converts the analog signal into a digital signal. In at least one embodiment, the sensing unit may include a digital filter with an input, wherein the input is connected to an output of the A/D converter and which filters the digital signal using a filter clock. In one or more embodiments, the filter clock is a multiple of the sampling clock for a specific period of time T.

In at least one embodiment, the period of time T may be adjustable. In at least one embodiment, the period of time T starts with the end of the separation of the sensing unit from the electrode during and after a stimulation pulse. In one or more embodiments, the filter clock during the period of time T may be twice to ten times the sampling clock.

In one or more embodiments, the analog signal may run through a pre-amplifier and an analog filter before sampling.

By way of at least one embodiment, the sensing unit may be a component of a tissue stimulator, such as a cardiac pacemaker, defibrillator, cardioverter or neurostimulator, which may be implantable devices.

Besides the sensing unit, according to one or more embodiments, the tissue stimulator may include at least one electrode connection, which is connected via a switch to the sensing unit and directly to a stimulation unit. In at least one embodiment, the tissue stimulator may include a clock generator that provides a sampling clock and a filter clock, and may include control unit connected to the switch, the sensing unit, the stimulation unit and the clock generator.

In one or more embodiments, the control unit of the tissue stimulator may trigger an opening of the switch at least for the duration of the delivery of one or more stimulation pulses, whereas the switch is closed outside this period.

In at least one embodiment, the control unit may trigger the clock generator to increase the filter clock and to maintain the sampling clock for a specific period of time T once the switch is closed again.

BRIEF DESCRIPTION OF THE DRAWINGS

The above and other aspects, features and advantages of at least one embodiment of the invention will be more apparent from the following more particular description thereof, presented in conjunction with the following drawings wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
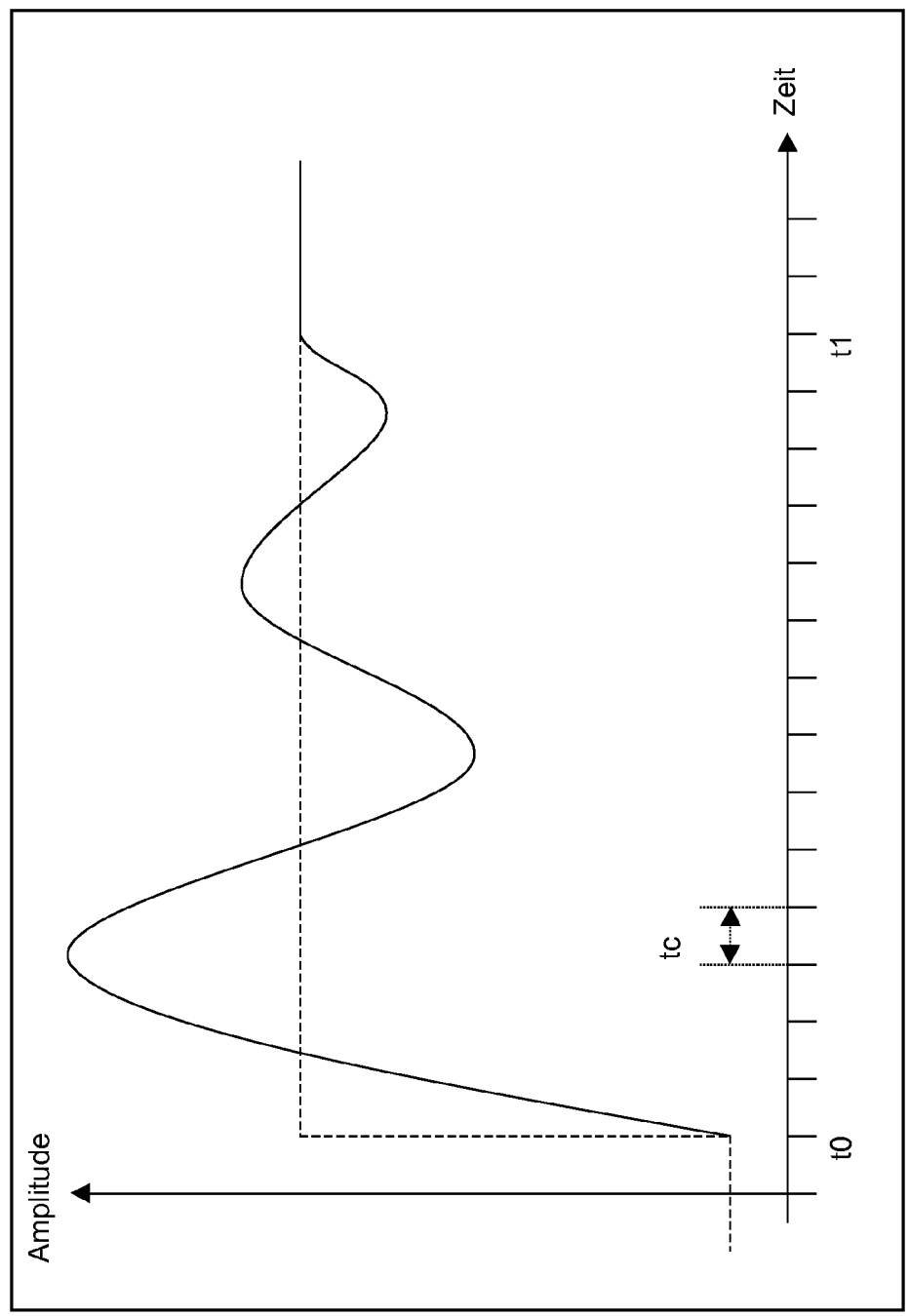
FIG. 1 shows the amplitude curve of the output signal of a digital filter.

FIG. 1 shows the amplitude curve of the output signal of a digital filter, according to one or more embodiments of the invention. By way of one or more embodiments, the digital filters may respond to a sudden change in the amplitude of the input signal, due to the principles involved, with an output signal illustrated by way of example in FIG. 1. In at least one embodiment, the amplitude of the filter input signal is illustrated as a dashed line and, at time t0, experiences a sudden change. In one or more embodiments, the output signal of the filter illustrated as a continuous line is characterized by a time-delayed rise in the amplitude to a value above the amplitude of the input signal and then again approximates the amplitude of the input signal at time t1. In at least one embodiment, the oscillation illustrated in FIG. 1 of the filter output signal is referred to as a transient process or as transient oscillation of the filter, and the time t1-t0 is referred to as the transient oscillation time, which may extend over a certain number of clock steps tc, for example as 14 clock steps tc. According to or more embodiments of the invention, the transient process or the transient oscillation time may be shortened by increasing the clock frequency of the filter for the period of time after an amplitude step at the input to a value that is a multiple of the clock frequency of the A/D converter. In at least one embodiment, the number of clock steps required for the transient process or for the transient oscillation of the filter may run through over a shorter period of time, and the output signal of the filter may be used earlier for signal detection.

Figure 2:
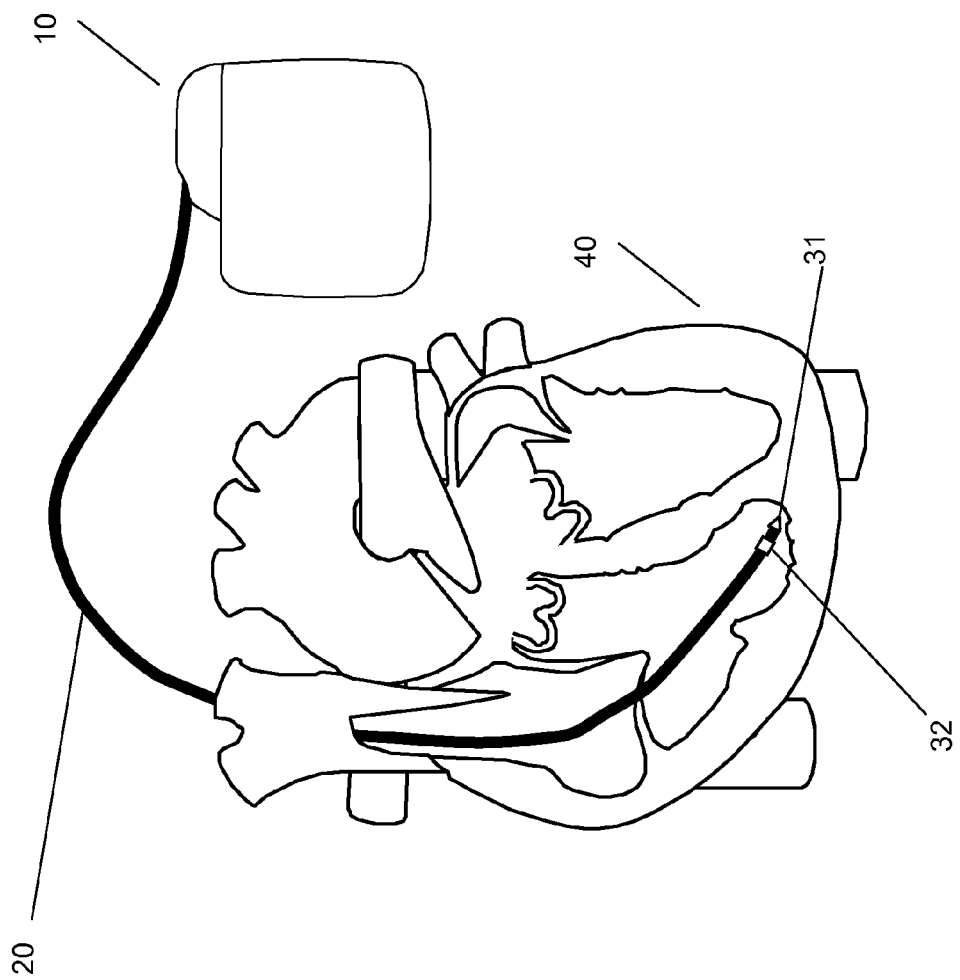
FIG. 2 shows a cardiac stimulator.

FIG. 2 shows a cardiac stimulator (10) connected, via an electrode connection, to an electrically conductive and insulated electrode line (20), according to one or more embodiments of the invention. In at least one embodiment, the distal end of the electrode line includes one or more electrodes (31, 32) that receive electric signals from the heart (40).

Figure 3:
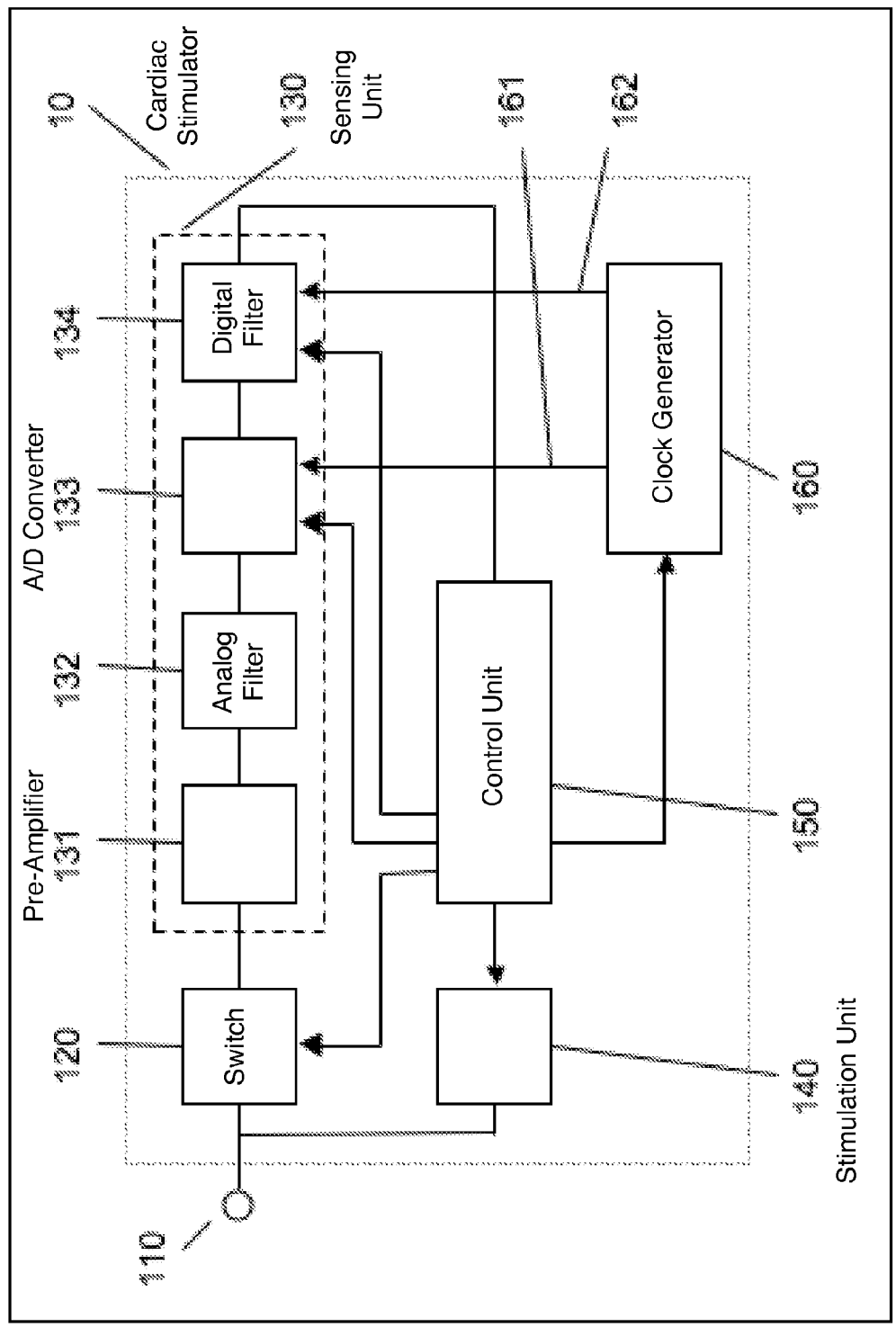
FIG. 3 shows the schematic structure of the cardiac stimulator.

FIG. 3 shows the further structure of the cardiac stimulator (10), according to one or more embodiments of the invention.

In one or more embodiments, the cardiac stimulator includes a sensing unit (130) and a stimulation unit (140), wherein the sensing unit (130) and the stimulation unit (140) are connected to and controlled by a control unit (150). In at least one embodiment of the invention, an input of the sensing unit (130) may be connected, via a switch (120) controlled by the control unit (150), to the electrode connection (110). In one or more embodiments, an output of the stimulation unit (140) may be connected to the electrode connection (110).

By way of one or more embodiments, the cardiac stimulator (10) may include an electric energy source (not illustrated in FIG. 3), for example a battery or an accumulator, which supplies energy to the sensing unit (130), the stimulation unit (140) and the control unit (150).

In at least one embodiment of the invention, the cardiac stimulator may include a clock generator (160), which provides clock signals and which may be controlled by the control unit (150).

In one or more embodiments, the sensing unit (130) may capture the electric signals of the heart received by the electrode and evaluates the electric signals to detect physiological events. For example, in at least one embodiment, electric signals from an electrode placed in the ventricle that are above a specific amplitude threshold value may be identified as natural contractions of the ventricle and may be forwarded to the control unit (150). In one or more embodiments, the control unit (150), in the absence of a natural contraction of the ventricle, may trigger the stimulation unit (140) to deliver one or more electric pulses to stimulate the heart. In at least one embodiment, during the delivery of a stimulation pulse, the control unit (150) may trigger the opening of the switch (120), which is otherwise closed, wherein the sensing unit (130) may be electrically disconnected from the electrode connection (110). After the delivery of the stimulation pulse, according to one or more embodiments, the control unit (150) may trigger the closing of the switch (120), wherein the sensing unit (130) may be connected to the electrode connection (110). In at least one embodiment, the switch (120) is also referred to herein as a blanking switch. In one or more embodiments, the disconnection of the sensing stage (130) from the electrode connection (110) is also referred to herein as analog blanking.

According to one or more embodiments, the sensing of electric signals of the heart and the stimulation may be implemented via two electrodes at the distal end of the electrode line, as illustrated in FIG. 2, and is referred to herein as bipolar signal acquisition or bipolar stimulation. In at least one embodiment, a unipolar signal acquisition or stimulation may be implemented, in which the electrode line may include only one electrode at the distal end, and wherein the electrically conductive housing of the cardiac stimulator (10) may replace the second electrode. In one or more embodiments, the cardiac stimulator may include a plurality of sensing and stimulation units.

The structure of the sensing unit (130) of FIG. 3 according to one or more embodiments of the invention will be discussed hereinafter.

In at least one embodiment, the input of the sensing unit (130) may be connected, via the blanking switch (120), to the electrode connection (110). In one or more embodiments, the electric signal received by the electrode runs through a pre-amplifier (131) and an analog filter (132), and may then be converted using an A/D converter (133) into a digital signal. The A/D converter (133), in at least one embodiment, may include an input for the sampling clock (161) necessary for the A/D conversion, wherein the sampling clock may be provided by the clock generator (160) and includes a sampling frequency. In at least one embodiment of the invention, the electric signal received by the electrode may first run through the analog filter (132) and then fed via the pre-amplifier (131) to the A/D converter (133). In one or more embodiments, the analog pre-amplifier (131) and the analog filter (132) may be omitted. In at least one embodiment, the digital signal at the output of the A/D converter (133) may be updated after each clock step to the time-discrete and amplitude-discrete sampling value of the analog input signal, and may then be filtered using a digital filter (134). In one or more embodiments, the digital filter (134) includes an input for a filter clock (162), wherein the filter clock (162) may be provided by the clock generator (160) and includes a filter frequency. By way of at least one embodiment, the output signal of the sensing unit (130) may be fed from the output of the digital filter (134) to a signal processing unit (not illustrated) for further processing. In one or more embodiments, the output of the signal processing unit is connected to the control unit (150). In at least one embodiment, the signal processing unit may be a component of the control unit (150).

According to one or more embodiments, the sensing unit (130) functions as follows:

When no stimulation pulse is delivered by the stimulation unit (140), the blanking switch (120) may be closed. In one or more embodiments, the A/D converter (133) and the digital filter (134) may obtain an identical sampling clock and filter clock from the clock generator (160) having the same sampling frequency and filter clock frequency. During the delivery of a stimulation pulse, in at least one embodiment, the blanking switch (120) may be opened and may be closed again after the delivery of a stimulation pulse and at the end of the programmable analog blanking time. As the blanking switch (120) is closed again, in at least one embodiment, the filter clock for the digital filter (134) may be increased by the clock generator for a certain number of clock pulses, and may then be reduced again to the original value, wherein the sampling clock for the A/D converter (133) remains unchanged. In one or more embodiments, the filter clock for the digital filter (134) may be increased directly after the delivery of a stimulation pulse.

By way of at least one embodiment, the filter with the transient oscillation behavior as illustrated in FIG. 1 requires 14 clock steps after the closure of the blanking switch for the transient process, which may lead to, in the case of an A/D converter having a sampling frequency of 500 Hz and a filter clock frequency of 500 Hz, to a period of time lasting 28 milliseconds for the digital blanking. As such, no bodily signals may be detected within 28 milliseconds after a stimulation pulse. If, according to one or more embodiments of the invention, the filter clock frequency for the first 14 clock steps is now increased after the closure of the blanking switch, for example by 8 times to 4000 Hz, the transient process will be completed after just 3.5 milliseconds, and therefore the digital blanking may be considerably reduced.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A sensing unit for a tissue stimulator wherein the sensing unit is a component of the tissue stimulator, the sensor unit comprising:
    an analog to digital (A/D) converter that samples an analog signal using a sampling clock and converts said analog signal into a digital signal,
        wherein said A/D converter comprises an output; and,
    a digital filter with an input;
        wherein the input is connected to the output of the A/D converter,
        wherein said digital filter comprises an input for a filter clock,
        wherein said digital signal at the output of the A/D converter is updated after each clock step to a time-discrete and amplitude-discrete sampling value of the analog signal,
        wherein said digital filter filters the digital signal using the filter clock, and
        wherein the filter clock is a multiple of the sampling clock for a specific period of time T.

2. The sensing unit according to claim 1, wherein the specific period of time T is adjustable.

3. The sensing unit according to claim 1, wherein the specific period of time T starts with an end of a stimulation pulse.

4. The sensing unit according to claim 1, wherein the filter clock is twice to ten times the sampling clock during the specific period of time T.

5. The sensing unit according to claim 1, wherein the analog signal passes through a preamplifier and an analog filter before said A/D converter samples said analog signal.

6. A tissue stimulator comprising:
    a sensing unit comprising
        an analog to digital (A/D) converter;
            wherein said A/D converter samples an analog signal using a sampling clock and converts said analog signal into a digital signal, and
            wherein said A/D converter comprises an output; and,
        a digital filter with an input;
            wherein the input is connected to the output of the A/D converter,
            wherein said digital filter filters the digital signal using a filter clock, and
            wherein the filter clock is a multiple of the sampling clock for a specific period of time T;
    at least one electrode connection connected to the sensing unit via a switch and connected directly to a stimulation unit;
    a clock generator comprising said sampling clock and said filter clock; and,
    a control unit connected to the switch, the sensing unit, the stimulation unit, and the clock generator;
    wherein the control unit triggers an opening of the switch during a delivery period of one or more stimulation pulses, and wherein the switch is closed outside said delivery period, and
    wherein the control unit triggers the clock generator to increase the filter clock and to maintain the sampling clock during the specific period of time T once the switch is opened.

7. The tissue stimulator according to claim 6, wherein said tissue stimulator is a cardiac pacemaker, defibrillator, cardioverter or neurostimulator.

8. The tissue stimulator according to claim 7, wherein said tissue stimulator is an implantable device.

9. The tissue stimulator according to claim 6, wherein the specific period of time T is adjustable.

10. The tissue stimulator according to claim 6, wherein the specific period of time T starts with an end of a stimulation pulse.

11. The tissue stimulator according to claim 6, wherein the filter clock is twice to ten times the sampling clock during the specific period of time T.

12. The tissue stimulator according to claim 6, wherein the analog signal passes through a preamplifier and an analog filter before said A/D converter samples said analog signal.

13. The tissue stimulator according to claim 6, wherein said digital filter comprises an input for a filter clock, and wherein said digital signal at the output of the A/D converter is updated after each clock step to a time-discrete and amplitude-discrete sampling value of the analog signal.

14. The tissue stimulator according to claim 6, wherein the control unit triggers the clock generator to increase the filter clock for a certain number of clock pulses, and wherein after the certain number of clock pulses the control unit then reduces the filter clock to an original value.

* * * * *